United States Patent [19]

Fuller

[11] Patent Number: 5,432,065
[45] Date of Patent: Jul. 11, 1995

[54] CYCLE SEQUENCING WITH NON-THERMOSTABLE DNA POLYMERASES

[75] Inventor: Carl W. Fuller, Cleveland Heights, Ohio

[73] Assignee: United States Biochemical Corporation, Cleveland, Ohio

[21] Appl. No.: 40,306

[22] Filed: Mar. 30, 1993

[51] Int. Cl.$^6$ .............. C12P 19/34; C12Q 1/68; C07H 17/00
[52] U.S. Cl. .............. 435/91.1; 435/91.2; 435/91.21; 435/91.32; 435/6; 536/23.1; 536/24.33; 935/8; 935/16; 935/77
[58] Field of Search .............. 435/91.1, 91.2, 91.21, 435/91.32, 6; 536/23.1, 24.33; 935/8, 16, 77

[56] References Cited

U.S. PATENT DOCUMENTS

| | | | |
|---|---|---|---|
| 4,683,195 | 7/1987 | Mullis et al. | 435/6 |
| 4,749,647 | 6/1988 | Thomas et al. | 435/6 |
| 4,753,884 | 6/1988 | Kit et al. | 435/235 |
| 4,774,176 | 9/1988 | Gottleib | 435/6 |
| 4,868,115 | 9/1989 | Obayashi et al. | 435/188 |
| 4,960,690 | 10/1990 | Ellis et al. | 435/6 |
| 5,169,766 | 12/1992 | Schuster et al. | 435/91 |
| 5,340,714 | 8/1994 | Katsilometes | 435/6 |

FOREIGN PATENT DOCUMENTS 9008839 9/1990 WIPO .

OTHER PUBLICATIONS

Smith et al., "Using Cosolvents to Enhance PCR Amplification", *Amplifications, A Fosrum for PCR Users*, pp. 16–17.
Fuller, 216 *Methods in Enzymology* 329, 1992, "Modified T7 DNA Polymerase for DNA Sequencing".
Kieleczawa, J. et al., 258 *Science* 1787, 1992.

*Primary Examiner*—Margaret Parr
*Assistant Examiner*—Bradley Lounsbury Sisson
*Attorney, Agent, or Firm*—Lyon & Lyon

[57] ABSTRACT

Method for performing a cycled primer extension reaction by contacting a template DNA with a primer in the presence of sufficient glycerol or ethylene glycol to lower the melting temperature of template DNA and primer hybrids below 70° C. and a DNA polymerase under conditions in which the DNA polymerase can cause primer extensions and is stable to the temperature at which the reaction mixture is heated to denature the primer extension product from the template nucleic acid; and a kit suitable for use in cycle primer extension reaction including the necessary primers, buffers and enzymes required for the procedure, and glycerol.

3 Claims, No Drawings

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( x i ) SEQUENCE DESCRIPTION: SEQ ID NO: 1:
    GTTTCCCAG TCACGACGTT GTA    23

CYCLE SEQUENCING WITH NON-THERMOSTABLE DNA POLYMERASES

BACKGROUND OF THE INVENTION

This invention relates to methods for cycle sequencing.

Cycle sequencing is a procedure by which the nucleotide base sequence of a nucleic acid molecule is determined. The method involves repeatedly providing a DNA sequencing primer in the presence of deoxynucleoside triphosphates and one or more dideoxynucleoside triphosphates in a suitable buffer solution with the template DNA to be sequenced. Denaturation of the extended primer from the template DNA is achieved by periodic heating after periods at lower temperatures at which primer extension occurs. Generally, this procedure is carried out using a thermostable enzyme, such as *Thermus aquaticus* DNA polymerase (Taq), so that more polymerase need not be added after each heating step. That is, when the cycling is between a temperature of 37° C. and 95° C. non-thermostable enzymes, such as T7 DNA polymerase or Klenow fragment of DNA polymerase I are denatured, and must be added after each heating step at 95° C. In contrast, Taq is stable to heating at 95° C. and thus, requires no additional enzyme to be added at each cycle.

SUMMARY OF THE INVENTION

This invention concerns use of a denaturation reagent which is compatible with enzymes generally used in DNA sequencing reactions and, in particular, cycle sequencing reactions, such that the temperature used for denaturation in the cycle sequencing procedure can be lowered to a temperature compatible with non-thermostable enzymes having advantageous properties not found in thermostable enzymes. In addition, the reagent added may increase the stability of the enzymes used in the reaction so that higher temperatures than are tolerated by such enzymes in the absence of such a reagent can be tolerated. Specifically, glycerol or ethylene glycol is provided in a cycle sequencing reaction so that enzymes such as T7 DNA polymerase, Klenow, reverse transcriptase, Bca polymerase, and mutants of Klenow lacking exonuclease activity can be used in the cycle sequencing reaction, or in a polymerase chain reaction (PCR) amplification procedure, or other related procedures. Indeed, such enzymes can now be used in any procedure in which it is important to perform a cycling step where the reaction is heated from a lower temperature to a higher temperature and in which a primer extension reaction is desired, such as in DNA sequencing or DNA or RNA amplification procedures. An example of a cycle sequencing reaction is provided by Fuller, U.S. Ser. No. 07/938,335, filed Aug. 28, 1992, abandoned in favor of continuing application U.S. Ser. No. 08/227,702, filed Apr. 14, 1994, hereby incorporated by reference herein.

Specifically, applicant has determined that the melting point of DNA decreases by about 0.5° C. for each 1% concentration of glycerol or ethylene glycol. Thus, the melting point of many DNAs in 70% glycerol is only about 45° C., and may be lower if deazaguanine or deoxyinosine are substituted for deoxyguanine, or if α-thio nucleotides are used in place of oxygen-containing nucleotides. The product of such reactions can be run in standard sequencing gels or in the glycerol-tolerant gels described by Fuller, U.S. Ser. No. 07/928,852, filed Aug. 10, 1992, hereby incorporated by reference herein.

Thus, in a first aspect, the invention features a method for performing a cycled primer extension reaction by contacting a template DNA with a primer in the presence of between 10 and 50% (v/v) glycerol or ethylene glycol (which is sufficient to reduce the melting temperature of the DNA hybrid between the template and primer, e.g., to below 70° C.). A thermostable or a non-thermostable DNA polymerase is added under conditions in which the DNA polymerase can cause primer extension, and is active or stable at the temperature at which the reaction mixture is heated to denature the primer extension product from the template nucleic acid. This reaction is performed with heating to a temperature less than required in the absence of glycerol (e.g., below 95° C., preferably below 85° C., and most preferably below 70° C.). This contrasts with the work of Smith et al., *Amplifications*, p. 16, where high temperatures (96° C.) are used when 20% glycerol is added for a polymerase chain reaction procedure.

By "stable" is meant having a half life of more than 3 minutes at the maximum temperature used, e.g., 70° C. in the reaction conditions.

In preferred embodiments, the procedure involves use of denaturation temperatures as low as 50° C. in the presence of 30% glycerol. Such procedures can also be performed with up to 50% glycerol with a denaturation temperature of only 37°-40° C. In yet other preferred embodiments, the invention features cycle sequencing or polymerase chain reaction procedures.

In a related aspect, the invention features a kit suitable for use in cycle primer extension reaction procedures which include the necessary primers, buffers, pure solutions or mixed solutions of glycerol or ethylene glycol (or their equivalent) and enzymes required for the procedure.

Other features and advantages of the invention will be apparent from the following description of the preferred embodiments thereof, and from the claims.

DESCRIPTION OF THE PREFERRED EMBODIMENTS

Destabilizing Agents

A number of useful molecular biological techniques capitalize on the fact that duplex DNA can be denatured under one condition and that the denatured strands can be placed at another condition wherein they can re-anneal or bind in a sequence-specific manner to synthetic primers or probes. These techniques include the polymerase chain reaction (PCR) and cycle sequencing. Synthetic oligonucleotide primers are added in large molar excess to an experimental DNA. The mixture is heated to a temperature high enough to denature the DNA (typically 95° C.), then cooled to a temperature low enough for the primer to bind to the DNA. DNA synthesis can then be primed at the 3' end of the annealed primer. Repeated cycling of the process will yield multiple copies of the DNA sequence immediately 3' to the annealing site which makes detection of these sequences much easier and more accurate than other methods.

The PCR and cycle sequencing process have been limited by the stability of the enzymes used. Either the polymerase must be added freshly to each cycle or it must be stable enough to survive periodic heating to 95° C. This invention provides an alternative to these procedures, and involves use of a denaturing reagent which decreases the melting temperature of the DNA. Some DNA denaturing agents, e.g., urea and formamide, do decrease the melting temperature of DNA by about 0.5° C. for each 1% (vol/vol) concentration, but inactivate most enzymes and in particular, DNA polymerases. For instance, T7 DNA polymerase is completely inactive in 40% formamide or DMSO although it does retain almost half its activity in 20% formamide.

Other materials which destabilize duplex DNA include ethylene glycol and glycerol. The melting temperatures of both small oligonucleotides (analogous to primers) and genomic double-stranded DNA are decreased by glycerol. The magnitude of the decrease is 0.4°–0.5° C. for each 1% (vol/vol) increase in glycerol concentration.

These results indicate that PCR and cycle sequencing can indeed be accomplished with a denaturation temperature of about 60° C. (or at least below 90° C.) and a primer annealing temperature of about 45° C. (or lower). Finding enzymes (hereinafter referred to as non-thermostable) which tolerate these relatively moderate temperatures is much easier than finding ones which are stable above 90° C. (hereinafter referred to as thermostable).

The key denaturation event for cycle sequencing is to separate the newly-synthesized DNA strand from the template strand. Since the newly synthesized strand is made from nucleotides added to the reaction mixture, analogues of the nucleotides can be used to influence the melting temperature of the product duplex. Analogues such as 7-deaza-dGTP, 7-deaza-dATP, dITP, and 7-deaza-dITP could be used to further reduce the temperature required for denaturing the product.

DNA Polymerase Tolerates and is Stabilized by Glycerol and Glycol

Glycerol stabilizes some DNA polymerases without reducing their activity significantly. Modified T7 DNA polymerase retains a significant fraction (e.g., about 50%) of its activity even in 40% glycerol and in addition, is much more stable in the presence of glycerol. The stabilities of T7 DNA polymerase, two modified forms of this enzyme and that of the Klenow fragment of E. coli DNA polymerase I in 40% glycerol solution were determined. DNA polymerase (2 units) was heated to a desired temperature for 3 minutes in 20 µl of 40 mM Tris HCl, 20 mM MgCl$_2$, 50 mM NaCl and 40% glycerol. Assays were performed using 10 µl of this heated enzyme. Assays (100 µl) were performed using 40 mM Tris HCl (pH 7.5), 10 mM MgCl$_2$, 1 mM DTT, 0.3 mM each dNTP including $^3$H dTTP (20 cpm/pmol), 5 µg of M13mp18 DNA and 5 pmol of primer (5'-GTTTTCCCAGTCACGACGTTGTA (SEQ. ID. NO. 1)). Following 1 minute incubation at 37° C. acid insoluble $^3$H was determined. 100% activity was taken to be the activity of enzyme pre-incubated at 37° C. These enzymes were also found to be active in the presence of 40% glycerol although concentrations of 50–75% glycerol do inhibit modified T7 DNA polymerase.

Thus, glycerol has two effects on the materials present in PCR and cycle sequencing experiments. It destabilizes the duplex DNA and stabilizes the polymerase (relative to normal reaction conditions without glycerol). These effects together should make it possible to perform either PCR or cycle sequencing with a number of enzymes not generally regarded as thermostable.

Ethylene glycol also destabilizes duplex DNA, but does not have a strong stabilizing effect on T7 DNA polymerase. Ethylene glycol solutions, however, have much lower viscosity than glycerol solutions. Thus, it may be preferable to use a combination of glycerol and ethylene glycol in practice so that solution viscosity is not excessive while at the same time destabilizing the DNA and stabilizing the enzyme. For instance, the stability of T7 DNA polymerase in a solution containing 20% glycerol and 20% ethylene glycol is almost the same as the stability in 40% glycerol but the viscosity is much lower, making the solution easier to handle.

Other materials stabilize enzymes, e.g., N-methyl glycine (sarcosine) and potassium glutamate. These salts, at a concentration of 50–200 mM, greatly stabilize T7 DNA polymerase. Concentrations of potassium glutamate between 10 and 200 mM also stimulate T7 DNA polymerase activity. These salts will increase the melting temperature of DNA, but 0.2M only increases Tm by 3° C. Thus, the combination of glycerol and potassium glutamate or N-methyl glycine may be used to further stabilize DNA polymerases for use in cycle sequencing and PCR.

Two examples follow showing cycle sequencing with non-thermostable enzymes.

Example 1: Bca DNA Polymerase

Bca DNA polymerase (Takara Co.) is a moderately-thermostable DNA polymerase. With DNA synthesis under traditional conditions (no glycerol, 95° C. melting step) no synthesis is observed beyond that which occurs during the first cycle. In contrast, cycling in the presence of 40% glycerol allows the use of 30° C. lower denaturation temperatures. With a denaturation temperature of 65° C. and synthesis temperature of 45° C., synthesis continues beyond 15 cycles, accumulating significantly more signal intensity and sequence data than that obtained without cycling.

Specifically, incubations (30 µl) contained 2 µg M13mp18 DNA, 4 pmol FAM-tagged M13 "-21" 17-mer primer (ABI), 10 mM Tris HCl (pH 8.5), 10 mM MgCl$_2$, 100 µM dideoxyATP, 25 µM each dATP, dCTP, dTTP and 7-deaza-dGTP and 4 units of Bca polymerase (Takara). Some solutions also contained 40% glycerol. The reaction mixtures were placed in vials in a thermal cycler and cycled once (higher temperature first), then 5 µl samples were taken. Similar samples were taken after 5, 15 and 30 cycles. The 5 µl samples were mixed with 4 µl formamide and 5 µl of this solution loaded onto a denaturing, 6% polyacrylamide gel prepared with glycerol-tolerant buffer mounted in the ABI model 373A DNA sequencing apparatus. This instrument records DNA sequence bands as peaks of fluorescence. The heights of representative peaks corresponding to nucleotides approximately 50, 120 and 250 bases from the primer were measured for the products of both cycling reactions. In case of low-temperature cycling (65° C.–45° C.), the intensities of all the peaks increased as the number of cycles increased. For instance, the intensity of the peak approximately 50 bases from the primer measured only 13 arbitrary fluorescence units after 1 cycle, but increased to 1039 units after 5 cycles and 1817 units after 30 cycles. In the case of high-temperature cycling normally used for cycle sequencing (95° C.–70° C.) there was no increase in peak intensity beyond that obtained in the first cycle. The polymerase is inactivated by the high temperature during the first cycle.

Example 2: Klenow

Klenow DNA polymerase (large fragment of *E. coli* DNA polymerase I) is a non-thermostable DNA polymerase. Nevertheless, it remains active when exposed to 65° C. for 3 minutes in the presence of 40% glycerol. Cycle sequencing in the presence of 40% glycerol using this DNA polymerase is also effective. In fact, repeated cycling generates readable signal intensities using as little as 0.1 μg of template DNA.

Specifically, incubations (30 μl) contained 0.2 μg M13mp18 DNA, 4 pmol FAM-tagged M13 "-21" 17-mer primer (ABI), 40 mM Tris HCl (pH 7.5), 20 mM $MgCl_2$, 100 μM dideoxyATP, 5 μM each dATP, dCTP, dTTP and 7-deaza-dGTP, 40% glycerol and 10 units of Klenow DNA polymerase. The reaction mixtures were placed in vials in a thermal cycler and cycled once (higher temperature first), then 5 μl samples were taken. Similar samples were taken after 2, 5 and 10 cycles. The 5 μl samples were mixed with 4 μl formamide and 5 μl of this solution loaded onto a denaturing, 6% polyacrylamide DNA sequencing gel prepared with glycerol-tolerant buffer mounted in the ABI model 373A DNA sequencing apparatus (Fuller, U.S. Ser. No. 07/862,734, filed Apr. 3, 1992, entitled "Electrophoresis of Nucleic Acid Fragments", hereby incorporated by reference herein). The gel was run at a constant 35 watts. Peak intensities for one peak (band) approximately 100 bases from the primer were measured. The intensity increased with the number of cycles indicating that the polymerase continued to remain active and synthesize DNA for at least 10 cycles.

Example 3: PCR with Bca Polymerase

The polymerase Chain Reaction (PCR) is a process for amplifying specific DNA sequences. Incubations (100 μl) contained 10 mM Tris.HCl buffer (pH.85), 10 mM $MgCl_2$, 100 ng bacteriophage lambda DNA, 0.1 μM each of primer 01 and primer 02 (the sequence of these primers is not relevant, any such primers can be used in this example), 40% glycerol, 1.5 mM each of dGTP, dCTP, dATP, and dTTP and 4 units Bca polymerase. This incubation mixture was then subjected to 30 cycles of 80° C., 15 sec; 40° C., 30 sec; and 60° C., 120 sec. This yields a product DNA of the expected size as determined by agarose gel electrophoresis. Similar cycling of reaction mixtures without 40% glycerol did not yield specific product DNA. Furthermore, cycling of the mixture with 40% glycerol to 85° C. or to temperatures normally used for PCR (93°-95° C.) failed to give a specific product, perhaps because the polymerase is inactivated at this temperature.

Cycle Sequencing

Cycle sequencing includes most of the required elements of PCR except that a single primer is used, so amplification can at most be linear with the number of cycles. The addition of a second primer and omission of dideoxynucleotides should result in specific amplification of DNA sequences between the primers. Since the properties of Klenow are much better known than those of Taq DNA polymerase, use of this enzyme may have advantages over thermostable DNA polymerases, especially for creating very large PCR products or optimizing yields. Furthermore, the reduced temperature requirements simplify equipment used for PCR or cycle sequencing. Thus, this invention features use of such enzymes in the presence of glycerol or ethylene glycol, and optionally sarcosine or potassium glutamate, in such methods.

Other Methods

The ability to cycle at the lower temperatures discussed above allows practice of several new methods. For example, one is the use of T7 DNA polymerase or Klenow DNA polymerase in combination with single stranded binding protein (ssb) and multiple contiguous hexamer primers. This method uses the properties of ssb and hexamer primers at 0°-4° C. to obtain specific priming using 3 or more contiguous hexamers. The method should work well for DNAs the size of cosmids (50,000 base pairs) but this requires the use of large amounts of cosmid DNA (10-20 μg) and ssb for each reaction. Cycling such a reaction with a DNA polymerase which is active at 0°-4° C., such as Klenow or T7 DNA polymerase, will greatly improve the ability of the method, accommodate small and variable amounts of template DNA, and decrease the amount of ssb required.

Specifically, a cycle sequencing reaction can be performed in the present invention using several (e.g., three) small oligomers, e.g., hexamers, which together form a specific primer suitable for allowing primer extension in a specific manner. If such extension is performed in the presence of only 2 or 3 dNTPs then the extension reaction will be limited, and the extended 3' oligonucleotide can be readily designed to be extended to form a primer. This primer can then be used in a cycle sequencing procedure with Taq DNA polymerase, or any other DNA polymerase, as described herein. See Kieleczawa et al., 258 *Science* 1787, 1992, hereby incorporated by reference herein.

Cycling at lower temperatures allows the use of less thermostable labels for cycle sequencing or PCR. For instance, the dioxetanes used for chemiluminescent detection of DNA (lumiphos, etc.) are highly susceptible to thermal decomposition. Cycling at 95° C. is not possible, but relatively brief exposures to 65° C. should be possible.

Oil could be eliminated from PCR and cycle sequencing. The temperature needed in this invention never approaches the boiling point, so ordinary capped vials should suffice. The elaborate closures used for PCR robots such as the ABI catalyst should be unnecessary, and the sealing requirements greatly reduced. In fact, even open tubes or microtiter plates can be used for a limited number of cycles (20 cycles is only 4 minutes at 65° C.).

Other embodiments are within the following claims.

---

I claim:

1. Method for performing a cycled primer extension reaction comprising the steps of:

contacting a mixture of a template DNA with a primer in the presence of about 40% (v/v) glycerol (final concentration) to lower the melting temperature of template DNA and extended primer hybrids below 80° C., and a DNA polymerase selected from the group consisting of Bca and Klenow, under conditions in which the DNA polymerase can cause primer extension, and is stable to the temperature at which the reaction mixture is heated to denature the primer extension product from the template nucleic acid; and heating said mixture to a temperature suitable for said primer extension reaction but less than 95° C., and then to a temperature suitable for denaturing said template DNA from the extended primer.

2. The method of claim 1, wherein the procedure involves use of denaturation temperatures as low as 60° C. in the presence of 40% glycerol (final concentration).

3. The method of claim 1, wherein said heating step is repeated a plurality of times.

* * * * *